United States Patent
Sebillotte-Arnaud et al.

(10) Patent No.: US 6,894,012 B2
(45) Date of Patent: May 17, 2005

(54) FOAMING COMPOSITION BASED ON SILICA AND ON CATIONIC POLYMER

(75) Inventors: Laurence Sebillotte-Arnaud, L'Hay les Roses (FR); Dominique Bordeaux, Longpont sur Orge (FR)

(73) Assignee: L'Oreal, Paris (FR)

( * ) Notice: Subject to any disclaimer, the term of this patent is extended or adjusted under 35 U.S.C. 154(b) by 290 days.

(21) Appl. No.: 10/199,177

(22) Filed: Jul. 22, 2002

(65) Prior Publication Data

US 2003/0134761 A1 Jul. 17, 2003

(30) Foreign Application Priority Data

Jul. 20, 2001 (FR) ............................................ 01 09767

(51) Int. Cl.$^7$ .............................. C11D 1/72; C11D 3/08; C11D 3/37
(52) U.S. Cl. ........................ 510/136; 510/119; 510/128; 510/130; 510/131; 510/421; 510/475; 510/486; 510/504; 510/511
(58) Field of Search ................................ 510/119, 128, 510/136, 130, 131, 421, 475, 486, 504, 511

(56) References Cited

U.S. PATENT DOCUMENTS

| 4,534,892 | A | * | 8/1985 | Suzuki et al. ................ 510/416 |
| 5,512,277 | A | * | 4/1996 | Uemura et al. .......... 424/78.03 |
| 5,885,948 | A | * | 3/1999 | Glenn et al. ................. 510/130 |
| 6,274,128 | B1 | * | 8/2001 | Bergmann et al. .......... 424/70.1 |

FOREIGN PATENT DOCUMENTS

| DE | 201 458 | 7/1983 |
| DE | 199 37 917 | 2/2001 |
| EP | 0 559 375 | 9/1993 |
| EP | 0 761 205 | 3/1997 |
| WO | WO 00/40208 | 7/2000 |

OTHER PUBLICATIONS

Patent Abstracts of Japan; vol. 16, No. 261: Jun. 12, 1992 & JP 04 059716; Feb. 26, 1992.

* cited by examiner

*Primary Examiner*—Charles Boyer
(74) *Attorney, Agent, or Firm*—Oblon, Spivak, McClelland & Neustadt, P.C.

(57) ABSTRACT

The present application relates to a cleansing composition comprising, in a physiologically acceptable aqueous medium, (1) at least one foaming surfactant, (2) at least 1% by weight of at least one silica with respect to the total weight of the composition, (3) at least one oxyalkylated compound and (4) at least one polymer chosen from cationic polymers and amphoteric polymers.

The composition obtained has the consistency of a gel and gives a lather of very good quality. It can be used in particular in the cosmetic or dermatological field, as products for cleansing or removing make-up from the skin, eyes, scalp and/or hair, and/or to disinfect the skin and/or the scalp.

36 Claims, No Drawings

FOAMING COMPOSITION BASED ON SILICA AND ON CATIONIC POLYMER

The present invention relates to a rinsable foaming cleansing composition comprising a silica, a cationic and/or amphoteric polymer and an oxyalkylenated compound and to the use of the said composition, in particular in the cosmetic or dermatological field, as cleansing products or make-up-removing products for the skin, the eyes, the scalp and/or the hair, for treating the human skin and/or for disinfecting the skin and/or the scalp.

Cleansing the skin is very important in caring for the face. It must be as efficient as possible because greasy residues, such as excess sebum, the remnants of cosmetic products used daily and make-up products, accumulate in the folds of the skin and can block the pores of the skin and result in the appearance of spots.

One means for properly cleansing the skin is to use foaming cleansing products. The foaming cleansing products currently available commercially are provided in the form of foaming bars, gels or creams and they may or may not comprise soaps (fatty acid salts). Soap-comprising foaming products have the advantage of giving a creamy lather; however, some consumers blame these products for causing tautness due to their excessive detergency. There is a search to reduce the level of soap in order to have a product which is better tolerated. However, the product then has an inadequate viscosity.

Furthermore, soap-free foaming products are generally well tolerated. However, the foaming qualities are poorer than those obtained with the soap-comprising products. One way of improving the foaming qualities and of obtaining qualities similar to those of the soap-comprising products (soft and dense lather with small bubbles) is to introduce cationic polymers. However, cationic polymers have the disadvantage of leaving a film on the skin, which is reflected by "film-forming" or slippery rinsing. This type of rinsing is not appreciated by consumers as it gives the impression of poorly washed skin.

Thus, the need remains for rinsable foaming products which, even in the absence of soap, have the properties required for foaming products, namely good qualities of the lather obtained, while exhibiting good stability.

The Applicant Company has discovered, surprisingly, first, that the introduction of silica into foaming compositions comprising a cationic polymer makes it possible to significantly improve the rinsing while reducing the unpleasant feeling of slipperiness, whatever the type of cationic polymer, and, secondly, that the incompatibility between the cationic polymers and the silicas, which can result in heterogeneous and unstable products, can be overcome by virtue of the presence of oxyalkylenated compounds and in particular oxyethylenated compounds.

Thus, products combining silica, oxyalkylenated compound and cationic or amphoteric polymer are not only stable and homogeneous but also have good properties, that is to say that they rinse out better than those comprising polymers alone and that they give both a good foaming quality and good cosmetic properties.

To achieve this objective, the silica has to be present in a sufficient amount, this amount being at least 1% by weight with respect to the total weight of the composition.

In addition to the properties indicated above, some cationic polymers, such as polyquaternium-7, make possible a faster conversion of the product than the other polymers when spread over the skin. This is reflected by the formation of an opaque white film which is referred to as "white glove" or "covering power", which film is very homogeneous, has a high covering capability and no longer allows the colour of the skin to be distinguished. This property allows the consumer to achieve markedly better and faster visualisation of the region of application of the product and thus to achieve better cleansing of the skin.

The use is certainly known of silica in cleansing or detergent compositions. Thus, for example, the document U.S. Pat. No. 5,880,076 discloses a liquid detergent composition which can comprise silicas. The documents EP-A-550 281 and U.S. Pat. No. 5,389,279 mention silica as a powder which can be incorporated in the cleansing compositions. However, no document discloses combining a sufficient amount of silica, an oxyalkylenated compound and a cationic polymer to produce a foaming composition which, even in the absence of soap, very closely approaches the foaming qualities of a soap-comprising composition.

Thus, a subject-matter of the present application is a cleansing composition comprising, in a physiologically acceptable aqueous medium, (1) at least one foaming surfactant, (2) at least 1% by weight of at least one silica, with respect to the total weight of the composition, (3) at least one oxyalkylenated compound and (4) at least one polymer chosen from cationic polymers, amphoteric polymers and their blends.

The term "physiologically acceptable medium" is understood here to mean a medium which is compatible with the skin, mucous membranes, scalp, eyes and/or hair. Furthermore, it is an aqueous medium, that is to say a medium comprising water and preferably an amount of water of at least 35% by weight, for example ranging from 35 to 95% by weight and better still from 40 to 80% by weight, with respect to the total weight of the composition.

The compositions of the invention are foaming and rinsing cleansing compositions. They are provided in the form of a gel which may or may not flow under its own weight, that is to say which has a viscosity which can range, for example, from 5 poises to 250 poises (0.5 to 25 Pa·s) and preferably from 35 poises to 200 poises (3.5 to 20 Pa·s), the viscosity being measured at 25° C. with a Rheomat 180 measuring device at $200\,s^{-1}$, this device being equipped with a different rotor according to the viscosities, for example with a rotor 2 for ranges of viscosities of less than 7 poises, with a rotor 3 for ranges of viscosities of 2 to 40 poises and with a rotor 4 for ranges of viscosities of greater than 20 poises.

Silica

The silica can be chosen from hydrophilic silicas, hydrophobic silicas and their mixtures. The term "silica" is understood to mean, in the present application, both pure silicas (hydrophilic or hydrophobic) and particles coated with silica.

The amount of silica(s) in the composition of the invention, whether it is pure silica or particles coated with silica, has to be at least 1% by weight of active material to achieve the aim of the invention and it can range, for example, by weight of active material, from 1 to 15% by weight, better still from 2 to 10% by weight and even better still from 3 to 6% by weight, with respect to the total weight of the composition.

Hydrophilic Silicas

These silicas are preferably amorphous and they can be of pyrogenic origin or of precipitated origin. They can be provided in the pulverulent form or as an aqueous dispersion.

Pyrogenic hydrophilic silicas are obtained by continuous flame pyrolysis of silicon tetrachloride ($SiCl_4$) at 1000° C. in the presence of hydrogen and of oxygen.

Precipitated silicas are obtained by reaction of an acid with solutions of alkali metal silicates, preferably sodium silicate.

According to a preferred embodiment of the invention, the hydrophilic silica is chosen from silicas having a specific surface of 30 to 500 m$^2$/g, a number-average particle size ranging from 3 to 50 nm and a tamped density ranging from 40 to 200 and better still from 50 to 150 g/l. These are more particularly the hydrophilic silicas described in Tables (1) and (2) below, and their mixtures.

These silicas are commercially available from Degussa-Hüls.

TABLE (1)

| Trade name | Aerosil 90 | Aerosil 130 | Aerosil 150 | Aerosil 200 |
|---|---|---|---|---|
| Method of production | Pyrogenation | Pyrogenation | Pyrogenation | Pyrogenation |
| BET specific surface (m$^2$/g) | 90 ± 15 | 130 ± 25 | 150 ± 15 | 200 ± 15 |
| Average particle size (nm) | 20 | 16 | 14 | 12 |
| Tamped density (g/l) | Approximately 80 | Approximately 50 | Approximately 50 | Approximately 50 |
| Density of the silanol groups (OH/m$^2$) | 2–3 | 2–3 | 2–3 | 2–3 |
| pH at 4% in water | 3.6–4.5 | 3.6–4.5 | 3.6–4.3 | 3.6–4.3 |
| Comment | | | | Size of the aggregates: 10–30 and 200 μm |

TABLE (2)

| Trade name | Aerosil 300 | Aerosil 380 | Aerosil OX 50 | Silica FK 320 DS |
|---|---|---|---|---|
| Method of production | Pyrogenation | Pyrogenation | Pyrogenation | Precipitation |
| BET specific surface (m$^2$/g) | 300 ± 30 | 380 ± 30 | 50 ± 25 | 170 ± 25 |
| Average particle size (nm) | 7 | 7 | 40 | 18 |
| Tamped density (g/l) | Approximately 50 | Approximately 50 | Approximately 130 | Approximately 80 |
| Density of the silanol groups (OH/m$^2$) | 2–3 | 2–3 | 2–3 | — |
| pH at 4% in water | 3.6–4.5 | 3.6–4.5 | 3.8–4.5 | 6.3 |

It was also possible to use silica as an aqueous dispersion, and for example a dispersion of colloidal silica, such as the product sold under the name Bindzil 30/220® by Eka Chemicals, a colloidal dispersion of amorphous silica (size: 14 nanometres) in water (30/70).

The hydrophilic silica which can be used in the composition of the invention can also consist of a particle comprising a silica surface, for example a particle totally or partially covered with silica, in particular an inorganic particle totally or partially covered with silica, such as the silica beads comprising titanium oxide sold under the name Torayceram S-IT® by Toray; the silica-alumina microspheres comprising titanium oxide (size: 150 μm) sold under the name Z-Light-Sphere W 1012® by Zeelan; the amorphous precipitated synthetic silica/titanium oxide particles (size: 106–500 μm) sold under the name Neosil PC20S® by Crosfield; the Nylon 6/silica/titanium oxide fibres (length of 2 mm and thickness of 2 denier), sold under the name Fiberlon Y2® by Wackherr; the silica coated with titanium dioxide and covered with porous silica (85/5/10) (size: 0.6 μm) sold under the name ACS-0050510® by SACI-CFPA; the anatase titanium oxide nanomaterial treated with alumina and silica at 40% in water (size: 60 nm, monodisperse) sold under the name Mirasun TIW 60® by Rhodia Chimie CRA; the anatase titanium oxide nanomaterial (60 nm) coated with silica/alumina/cerium(IV) 15/5/3 as a 32% aqueous dispersion sold under the name Mirasun TIW 160® by Rhodia Chimie CRA; the anatase titanium oxide nanomaterial treated with alumina and silica (34/4.3/1.7) as a 40% aqueous dispersion sold under the name Tioveil AQ-N® by Uniqema; the titanium oxide nanomaterial coated with silica (66/33) (particle size of the titanium dioxide: 30 nm; silica thickness: 4 nm) sold under the name Maxlight TS-04® by Nichimen Europe plc; and the titanium oxide nanomaterial coated with silica (80/20) (titanium dioxide particle size: 30 nm; silica thickness: 2 nm) sold under the name Maxlight TS-042® by Nichimen Europe plc. These particles can also have optical properties in the product and on the skin. For example, they can have a mattifying or slightly whitening effect.

Use is preferably made, as hydrophilic silica, of pyrogenic silicas and in particular those sold under the names Aerosil 200® and Aerosil 300® by Degussa-Hüls.

Hydrophobic Silicas

Amorphous hydrophobic silicas of pyrogenic origin are obtained from hydrophilic silicas. As described above, the latter are obtained by continuous flame pyrolysis of silicon tetrachloride (SiCl$_4$) at 1000° C. in the presence of hydrogen and of oxygen. They are subsequently rendered hydrophobic by treatment with halogenated silanes, alkoxysilanes or silazanes. Hydrophobic silicas differ from the starting hydrophilic silicas, inter alia, in a lower density of silanol groups and in a smaller water vapour adsorption.

According to a preferred embodiment of the invention, the hydrophobic silica is chosen from silicas having a specific surface of 50 to 500 m$^2$/g, a number-average particle size ranging from 3 to 50 nm and a tamped density ranging from 40 to 200 and better still from 50 to 150 g/l. These are more particularly the hydrophobic silicas described in Table (3) below, and their mixtures. These silicas are commercially available from Degussa-Hüls.

TABLE (3)

| Trade name | Aerosil R202 | Aerosil R805 | Aerosil R812 | Aerosil R972 | Aerosil R974 |
|---|---|---|---|---|---|
| BET specific surface (m$^2$/g) | 90 ± 20 | 150 ± 25 | 260 ± 30 | 110 ± 20 | 170 ± 20 |
| Average particle size (nm) | 14 | 12 | 7 | 16 | 12 |
| Tamped density (g/l) | Approximately 50 | Approximately 50 | Approximately 50 | Approximately 50 | Approximately 50 |
| pH at 4% in water | 4–6 | 3.5–5.5 | 5.5–7.5 | 3.6–4.3 | 3.4–4.2 |

The hydrophobic silica which can be used in the composition of the invention can also consist of a particle totally or partially covered with silica, in particular an inorganic particle totally or partially covered with hydrophobic silica, such as pigments and metal oxides covered with hydrophobic silica. These particles can also have optical properties in the product and on the skin; for example, they can have a mattifying or slightly whitening effect.

Use is preferably made, as hydrophobic silica, of that sold under the name Aerosil R972® by Degussa-Hüls.

Oxyalkylenated Compounds

The oxyalkylenated compound or compounds which can be used in the composition of the invention can comprise ethylene oxide groups (oxyethylenated compounds), propylene oxide groups (oxypropylenated compounds) or both (oxyethylenated/oxypropylenated compounds).

Use may be made of one or more oxyalkylenated compounds and the amount of oxyalkylenated compound(s) in the composition of the invention can range, for example, by weight of active material, from 0.1 to 20% by weight, preferably from 0.5 to 10% by weight and better still from 1 to 5% by weight, with respect to the total weight of the composition.

The oxyalkylenated compounds can be chosen in particular from polyethylene glycols, derivatives of polyethylene glycol and/or polypropylene glycol, oxyethylenated/oxypropylenated copolymers, polyol alkoxylated alkyl or acyl derivatives, triesters of glycerol and of oxyalkylenated and in particular oxyethylenated fatty acids, ethoxyethylenated urethane derivatives modified by alkyl chains, and their mixtures.

According to a preferred embodiment of the invention, the oxyalkylenated compound comprises at least 10 oxyethylene units, also known as ethylene oxide units.

1. The polyethylene glycols which can be used in the composition of the invention are ethylene oxide polycondensates having a number of ethylene oxide (EO) units of greater than 10. The ethylene oxide number can range, for example, from 10 to 50 000 and preferably from 14 to 10 000. Mention may be made, as polyethylene glycols, of, for example, polyethylene glycol comprising 7 000 EO (CTFA name: PEG-7M), such as the product sold under the name Polyox WSR N-750® by Amerchol, polyethylene glycol comprising 75 EO (CTFA name: PEG-75), polyethylene glycol comprising 20 000 EO (CTFA name: PEG-20M), such as the product sold under the name Polyox WSR 1105® by Amerchol, or polyethylene glycol comprising 150 EO (CTFA name: PEG-150).

2. The derivatives of polyethylene glycol and/or of polypropylene glycol are condensates of polyethylene and/or polypropylene glycol with one or more fatty acids or fatty alcohols. These are compounds of formula (I):

$$R\text{—}(EO)_m\text{—}(PO)_n\text{—}R' \qquad (I)$$

in which $0 \leq m \leq 300$ and $0 \leq n \leq 300$, and $m+n \geq 6$, R and R' represent, independently of one another, a saturated or unsaturated, linear or branched and hydroxylated or non-hydroxylated alkyl, acyl or aralkyl chain comprising from 1 to 26 carbon atoms and preferably from 12 to 20 carbon atoms, or an aryl chain.

These derivatives can, for example, be esters of fatty acids and of polyethylene glycol and/or of polypropylene glycol, and ethers of fatty alcohols and of polyethylene glycol and/or of polypropylene glycol.

Mention may be made, as esters of fatty acids and of polyethylene glycol and/or polypropylene glycol, of, for example, polyethylene glycol (150 EO) distearate, such as the product sold under the name Atlas G-1821® by Uniqema, polyethylene glycol (250 EO) distearate, such as the product sold under the name Emanon 3299R® by Kao, PEG-150 dibehenate, such as the product sold under the name Ethox PEG 6000 Dibehenate® by Ethox, polyethylene glycol (120 EO) palmitostearate, such as the product sold under the name Stearate 6000 WL 1644® by Gattefosse, copolymer of polyethylene glycol (30 EO) and of 12-hydroxystearic acid, such as the product sold under the name Arlacel P135® by Uniqema, or polyethylene glycol (40 EO) stearate, such as the product sold under the name Myrj 52® by Uniqema.

Mention may in particular be made, as examples of polyethylene glycol ethers, of oxyethylenated (30 EO) cetyl alcohol, such as the product sold under the name Nikkol BC-30TX® by Nikkol, oxyethylenated (15 EO) oleyl alcohol, such as the product sold under the name Nikkol BO-15TX® by Nikkol, oxyethylenated (50 EO) oleyl alcohol, such as the product sold under the name Nikkol BO-50® by Nikkol, oxyethylenated (10 EO) behenyl alcohol, such as the product sold under the name Mergital B 10® by Nikkol, oxyethylenated (30 EO) behenyl alcohol, such as the product sold under the name Nikkol BB-30® by Nikkol, oxyethylenated (12 EO) lauryl alcohol, such as the product sold under the name Rewopal 12® by Goldschmidt, oxyethylenated (23 EO) lauryl alcohol, such as the product sold under the name Simulsol P 23® by Seppic, oxyethylenated (20 EO) 2-octyldodecyl alcohol, such as the product sold under the name Octyldodeceth-20® by Stearinerie Dubois, oxyethylenated (20 EO) isocetyl alcohol, such as the product sold under the name Arlasolve 200 US® by Uniqema, oxyethylenated (10 EO) oleyl alcohol, such as the product sold under the name Brij 97® by Uniqema, oxyethylenated (20 EO) oleyl alcohol, such as the product sold under the name Brij 98® by Uniqema, oxyethylenated (100 EO) stearyl alcohol, such as the product sold under the name Brij 700® by Uniqema, or oxyethylenated (21 EO) stearyl alcohol, such as the product sold under the name Brij 721® by Uniqema.

Mention may in particular be made, as examples of polyethylene glycol/polypropylene glycol ethers, of oxyethylenated (20 EO) oxypropylenated (5 PO) cetyl alcohol, such as the product sold under the name Procetyl AWS® by Croda, oxyethylenated (26 EO) oxypropylenated (26 PO) butyl alcohol, such as the product sold under the name PPG-26-Buteth-26® by Goldschmidt, oxyethylenated (26 EO) oxypropylenated (26 PO) butyl alcohol, such as the product sold under the name Varonic APEB® by Goldschmidt, oxyethylenated (30 EO) oxypropylenated (6 PO) decyltetradecanol such as the product sold under the name Nikkol PEN-4630® by Nikkol, or oxyethylenated (25 EO) oxypropylenated (25 PO) lauryl alcohol, such as the product sold under the name ADF-Oleile® by Vevy.

3. Mention may be made, as oxyethylenated/oxypropylenated copolymers, of, for example, the polyoxyethylene/polyoxypropylene (17 EO/6 PO) random copolymer sold under the reference Ucon 75-H-450® by Amerchol. The molecules comprising more EO and/or more PO are not excluded.

4. The polyol ethoxylated alkyl or acyl derivatives can, for example, be oxyethylenated derivatives of esters of fatty acids or of ethers of fatty alcohol and of polyol, such as glycerol, sorbitol, glucose or pentaerythritol.

Mention may be made, as derivatives of this type, of, for example, oxyethylenated (78 EO) glyceryl cocoate, such as the product sold under the name Simulsol CG by Seppic, oxyethylenated (120 EO) methyl glucose dioleate, such as the product sold under the name Glucamate DOE-120 Végétal® by Amerchol, oxyethylenated (40 EO) sorbitan septaoleate, such as the product sold under the name Arlatone T® by Uniqema, oxyethylenated (10 EO) polyglyceryl (2 mol of glycerol) laurate, such as the product sold under the name HOE S 3495® by Clariant, oxyethylenated (60 EO) glyceryl isostearate, such as the product sold under the name Emalex GWIS-160® by SACI-CFPA, oxyethylenated (20 EO) glyceryl monostearate, such as the product sold under the name Cutina E 24® by Cognis, oxyethylenated (200 EO) glyceryl stearate, such as the product sold under the name Simulsol 220 TM® by Seppic, or oxyethylenated (150 EO) pentaerythrityl tetrastearate, such as the product sold under the name Crothix® by Croda.

5. Mention may be made, as triesters of glycerol and of oxyalkylenated and in particular oxyethylenated fatty acids, of, for example, oxyethylenated (50 EO) olive oil, such as the product sold under the name Crovol O-70® by Croda.

6. Mention may be made, as ethoxyethylenated urethane derivatives modified by alkyl chains, of, for example, those of formulae (II) and (III):

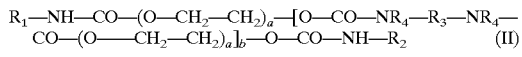
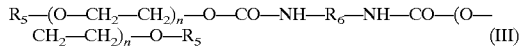

in which the $R_1$, $R_2$ and $R_5$ radicals represent an alkyl group comprising from 1 to 18 carbon atoms; $R_3$ and $R_6$ represent a linear, cyclic or aromatic hydrocarbonaceous radical comprising from 4 to 36 carbon atoms; $R_4$ represents a hydrogen atom or an alkyl radical comprising from 1 to 6 carbon atoms, preferably a hydrogen atom; a is an integer ranging from 90 to 600, b is an integer ranging from 1 to 4, and n is an integer ranging from 10 to 300.

Mention may be made, for example, of the water-soluble polymers obtained by an addition reaction of diisocyanates (HMDI: hexamethylene diisocyanate) with diols (polyethers, polyesters) and terminated by hydrophobic groups originating from ethoxylated or ethoxylated/propoxylated fatty alcohols, such as the oxyethylenated (100 EO) stearyl alcohol/polyethylene glycol (136 EO)/hexamethylene diisocyanate copolymer sold under the name Serad FX 1100 by Adriss.

Mention may also be made, for example, of the products sold under the names Acrysol 44 (or Aculyn 44) and Acrysol 46 (Aculyn 46) (CTFA name: PEG-150/Decyl Alcohol/SMDI Copolymer) by,Rohm & Haas, which are polyurethanes obtained by condensation of hexamethylene diisocyanate and of polyethylene glycol, carrying a methyl residue and an octadecyl residue respectively at their ends. These polyurethanes additionally comprise from 3 to 5% by weight of an enzymatically modified starch matrix. Mention may also be made of the products sold under the names Rheolate® 205, 210, 212, 216, 244, 278, 255, 266, 288, 300 or 350 by Elementis or the products sold under the names Borchigel LW.44, L.75. N, L 76, VP 9628-LL36, VP 97105-NT40 or VP 9620 by Borchers.

The preferred compounds among the abovementioned oxyethylenated compounds are in particular the esters of fatty acids and of polyethylene glycol and/or polypropylene glycol and in particular polyethylene glycol (150 EO) distearate, polyethylene glycol (250 EO) distearate, PEG-150 dibehenate and polyethylene glycol (120 EO) palmitostearate; the polyol ethoxylated alkyl or acyl derivatives and in particular oxyethylenated (120 EO) methyl glucose dioleate and oxyethylenated (150 EO) pentaerythrityl tetrastearate; the ethoxyethylenated urethane derivatives modified by alkyl chains and in particular the oxyethylenated (100 EO) stearyl alcohol/polyethylene glycol (136 EO)/hexamethylene diisocyanate copolymer sold under the name Serad FX 1100 by Adriss; and their mixtures.

Foaming Surfactants

The cleansing composition according to the invention constitutes a foaming composition and it comprises at least one foaming surfactant which will contribute the foaming nature to the composition. This surfactant can be chosen from any nonionic, anionic, amphoteric and zwitterionic foaming surfactant, and mixtures thereof.

The amount of surfactant(s) can range, for example, by way of active material, from 2 to 50% by weight and better still from 3 to 30% by weight, with respect to the total weight of the composition.

1. Nonionic Surfactants

Use may be made, for example, as nonionic surfactants, of alkylpolyglucosides (APG), maltose esters, polyglycerolated fatty alcohols, glucamine derivatives, such as 2-ethylhexyloxycarbonyl-n-methylglucamine, and their mixtures.

Use is preferably made, as alkylpolyglucosides, are those comprising an alkyl group comprising from 6 to 30 carbon atoms and preferably from 8 to 16 carbon atoms and comprising a hydrophilic (glucoside) group preferably comprising 1.2 to 3 saccharide units. Mention may be made, as alkylpolyglucosides, of, for example, decylglucoside (($C_9$/$C_{11}$ alkyl)polyglucoside (1,4)), such as the product sold under the name Mydol 10® by Kao Chemicals, under the name Plantaren 2000 UP® by Henkel and under the name Oramix NS 10® by Seppic; caprylyl/caprylglucoside, such as the product sold under the name Oramix CG 110® by Seppic; laurylglucoside, such as the products sold under the names Plantaren 1200 N® and Plantacare 1200® by Henkel; and cocoglucoside, such as the product sold under the name Plantacare 818/UP® by Henkel.

The maltose derivatives are, for example, those disclosed in the document EP-A-0 566 438, such as 6'-(O-octanoyl)-D-maltose, or alternatively 6'-(O-dode-canoyl)-D-maltose, disclosed in the document FR-A-2 739 556.

Mention may be made, among polyglycerated fatty alcohols, of polyglycerated dodecanediol (3.5 mol of glycerol), a product manufactured under the name Chimexane NF® by Chimex.

2. Anionic Surfactants

Use may be made, as anionic surfactants, of, for example, carboxylates, amino acid derivatives, alkyl sulphates, alkyl ether sulphates, sulphonates, isethionates, taurates, sulphosuccinates, alkyl sulphoacetates, phosphates and alkyl phosphates, polypeptides, anionic alkylpolyglucoside derivatives, fatty acid soaps, and their mixtures. While fatty acid soaps can be added to the composition of the invention, their amount must be such that their addition does not prejudice the cosmetic qualities of the composition obtained.

Mention may be made, as carboxylates, of, for example, alkaline salts of N-acylamino acids; amido ether carboxylates (AEC), such as sodium lauryl amido ether carboxylate (3 EO), sold under the name Akypo Foam 30® by Kao Chemicals; polyoxyethylenated carboxylic acid salts, such as oxyethylenated (6 EO) sodium lauryl ether carboxylate (65/25/10 $C_{12}$–$C_{14}$–$C_{16}$) sold under the name Akypo Soft 45 NV® by Kao Chemicals; polyoxyethylenated and carboxymethylated olive oil fatty acids, such as the product sold under the name Olivem 400® by Biologia E Tecnologia; or oxyethylenated (6 EO) sodium tridecyl ether carboxylate, sold under the name Nikkol ECTD-6NEX® by Nikkol.

The amino acid derivatives can be chosen, for example, from sarcosinates and in particular acylsarcosinates, such as sodium lauroylsarcosinate, sold under the name Sarkosyl NL 97® by Ciba or under the name Oramix L 30® by Seppic, sodium myristoyl-sarcosinate, sold under the name Nikkol Sarcosinate MN® by Nikkol, or sodium palmitoylsarcosinate, sold under the name Nikkol Sarcosinate PN® by Nikkol; alaninates, such as sodium N-lauroyl-N-methylamidopropionate, sold under the name Sodium Nikkol Alaninate LN 30® by Nikkol or under the name Alanone Ale® by Kawaken, and triethanolamine N-lauroyl- N-methylalanine, sold under the name Alanone Alta® by Kawaken; N-acylglutamates, such as triethanolamine monococoylglutamate, sold under the name Acylglutamate CT-12® by Ajinomoto, and triethanolamine lauroylglutamate, sold under the name Acylglutamate LT-12® by Ajinomoto; aspartates, such as the mixture of triethanolamine N-lauroylaspartate and of triethanolamine N-myristoylaspartate sold under the name Asparack® by Mitsubishi; citrates, and their mixtures.

Mention may be made, as alkyl ether sulphates, of, for example, sodium lauryl ether sulphate (70/30 $C_{12}$–$C_{14}$) (2.2 EO), sold under the names Sipon AOS 225® or Texapon N702 Paté® by Henkel, ammonium lauryl ether sulphate (70/30 $C_{12}$–$C_{14}$) (3 EO), sold under the name Sipon LEA 370® by Henkel, or ammonium ($C_{12}$–$C_{14}$)alkyl ether (9 EO) sulphate, sold under the name Rhodapex AB/20® by Rhodia Chimie.

Mention may be made, as sulphonates, of, for example, alpha-olefin sulphonates, such as sodium alpha-olefin sulphonate ($C_{14}$–$C_{16}$), sold under the names Bio-Terge AS-40® and Bio-Terge AS-40 CG® by Stepan under the names Witconate AOS Protégé® and Sulframine AOS PH 12® by Witco, secondary sodium olefin sulphonate, sold under the name Hostapur SAS 30® by Clariant; or linear alkylaryl sulphonates, such as sodium xylene sulphonate, sold under the names Manrosol SXS30®, Manrosol SXS40® and Manrosol SXS93® by Manro.

Mention may be made, as isethionates, of acylisethionates, such as sodium cocoylisethionate, for example the product sold under the name Jordapon CI P® by Jordan.

Mention may be made, as taurates, of the sodium salt of palm kernel oil methyltaurate, sold under the name Hostapon CT Paté® by Clariant; N-acyl-N-methyltaurates, such as sodium N-cocoyl-N-methyl-taurate, sold under the name Hostapon LT-SF® by Clariant or sold under the name Nikkol CMT-30-T® by Nikkol, or sodium palmitoyl methyltaurate, sold under the name Nikkol PMT® by Nikkol.

Mention may be made, as sulphosuccinates, of, for example, oxyethylenated (3 EO) lauryl (70/30 $C_{12}$–$C_{14}$) alcohol monosulphosuccinate, sold under the names Setacin 103 Special® and Rewopol SB-FA 30 K 4® by Witco, the disodium salt of a hemisulphosuccinate of $C_{12}$–$C_{14}$ alcohols, sold under the name Setacin F Special Paste® by Zschimmer Schwarz, oxyethylenated (2 EO) disodium oleamidosulphosuccinate, sold under the name Standapol SH 135® by Henkel, oxyethylenated (5 EO) lauramide monosulphosuccinate, sold under the name Lebon A-5000® by Sanyo, the disodium salt of oxyethylenated (10 EO) lauryl citrate monosulphosuccinate, sold under the name Rewopol SB CS 50® by Witco, or ricinoleic monoethanolamide monosulphosuccinate, sold under the name Rewoderm S 1333® by Witco.

Mention may be made, as phosphates and alkyl phosphates, of, for example, monoalkyl phosphates and dialkyl phosphates, such as lauryl monophosphate, sold under the name MAP 20® by Kao Chemicals, the potassium salt of dodecyl phosphate, a mixture of mono- and diester (predominantly diester) sold under the name Crafol AP-31® by Cognis, the mixture of octyl phosphate monoester and diester, sold under the name Crafol AP-20® by Cognis, the mixture of ethoxylated (7 mol of EO) 2-butyloctyl phosphate monoester and diester sold under the name Isofol 12 7 EO-Phosphate Ester® by Condea, the potassium or triethanolamine salt of mono($C_{12}$–$C_{13}$)alkyl phosphate, sold under the references Arlatone MAP 230K-40® and Arlatone MAP 230T-60® by Uniqema, or potassium lauryl phosphate, sold under the name Dermalcare MAP XC-99/09® by Rhodia Chimie.

The polypeptides are obtained, for example, by condensation of a fatty chain with cereal amino acids and in particular wheat and oat amino acids. Mention may be made, as polypeptides, of, for example, the potassium salt of hydrolysed lauroyl wheat protein, sold under the name Aminofoam W OR® by Croda; the triethanolamine salt of hydrolysed cocoyl soybean protein, sold under the name May-Tein SY® by Maybrook; the sodium salt of oat lauroyl amino acids, sold under the name Proteol Oat® by Seppic; collagen hydrolysate grafted to coconut fatty acid, sold under the name Geliderm 3000® by Deutsche Gelatine; or soybean proteins acylated with hydrogenated coconut acids, sold under the name Proteol VS 22® by Seppic.

The anionic alkylpolyglucoside derivatives can in particular be citrates, tartrates, sulphosuccinates, carbonates and glycerol ethers obtained from alkylpolyglucosides. Mention may be made, for example, of the sodium salt of cocoylpolyglucoside (1,4) tartaric ester, sold under the name Eucarol AGE-ET® by Cesalpinia; the disodium salt of cocoylpolyglucoside (1,4) sulphosuccinic ester, sold under the name Essai 512 MP® by Seppic; or the sodium salt of cocoylpolyglucoside (1,4) citric ester, sold under the name Eucarol AGE-EC® by Cesalpinia.

The fatty acid soaps which can be used as anionic surfactants are fatty acids of natural or synthetic origin, salified with an inorganic or organic base. The fatty chain can comprise from 6 to 22 carbon atoms, preferably from 8 to 18 carbon atoms. The inorganic or organic base can be chosen from hydroxides of alkali metals or alkaline earth metals, amino acids and aminoalcohols. Use may be made, as salts, of, for example, sodium, potassium, magnesium, triethanolamine, N-methylglucamine, lysine and arginine salts. Mention may be made, as soaps, of, for example, the potassium or sodium salts of lauric acid, myristic acid, palmitic acid or stearic acid (potassium or sodium laurate, myristate, palmitate and stearate), and their mixtures.

3. Amphoteric and Zwitterionic Surfactants

Use may be made, as amphoteric and zwitterionic surfactants, of, for example, betaines, N-alkylamidobetaines and their derivatives, glycine derivatives, sultaines, alkyl polyaminocarboxylates, alkylamphoacetates, and their mixtures.

Mention may be made, as betaines, of, for example, cocobetaine, such as the product sold under the name Dehyton AB-30® by Henkel; laurylbetaine, such as the product sold under the name Genagen KB® by Clariant; oxyethylenated (10 EO) laurylbetaine, such as the product sold under the name Laurylether(10 EO)betaine® by Shin Nihon Rica; or oxyethylenated (10 EO) stearylbetaine, such as the product sold under the name Stearylether(10 EO)betaine® by Shin Nihon Rica.

Mention may be made, among N-alkylamidobetaines and their derivatives, of, for example, cocamidopropyl betaine, sold under the name Lebon 2000 HG® by Sanyo or under the name Empigen BB® by Albright & Wilson; or lauramidopropyl betaine, sold under the name Rewoteric AMB12P® by Witco.

Mention may be made, as glycine derivatives, of sodium N-cocoylglycinate, sold under the name Amilite GCS-12® by Ajinomoto.

Mention may be made, as sultaines, of cocoylamidopropylhydroxysulphobetaine, sold under the name Crosultaine C-50® by Croda.

Mention may be made, as alkyl polyaminocarboxylates (APAC), of sodium cocoylpolyaminocarboxylate, sold under the name Ampholak 7 CX/C® and Ampholak 7 CX® by Akzo Nobel; sodium stearylpolyamidocarboxylate, sold under the name Ampholak 7 TX/C® by Akzo Nobel; or sodium carboxymethyloleylpolypropylamine, sold under the name Ampholak XO7/C® by Akzo Nobel.

Mention may be made, as alkylamphoacetates, of, for example, N-disodium N-cocoyl-N-carboxymethoxyethyl-N-(carboxymethyl)ethylenediamine (CTFA name: disodium cocamphodiacetate), such as the product sold under the name Miranol C2M ConcentréNP® by Rhodia Chimie; and N-sodium N-cocoyl-N-hydroxyethyl-N-(carboxymethyl)ethylenediamine (CTFA name: sodium cocamphoacetate).

Among the abovementioned surfactants according to a specific embodiment of the invention, use is more particularly made, as anionic surfactants, of acylsarcosinates, oxyethylenated alkyl ether sulphates, N-acyl-N-methyltaurates, N-acylglutamates, acylisethionates, sulphosuccinates, phosphates and alkyl phosphates, or polypeptides; as amphoteric and zwitterionic surfactants, of betaines and alkylamphoacetates; as nonionic surfactants, of alkylpolyglucosides, 6'-(O-octanoyl)-D-maltose, 6'-(O-dodecanoyl)-D-maltose, polyglycerolated dodecanediol (3.5 mol of glycerol) or 2-ethylhexyloxycarbonyl-N-methylglucamine; and of the mixtures of these surfactants.

According to an even more particularly preferred embodiment of the invention, the surfactants are chosen from phosphates and alkyl phosphates, alkylpolyglucosides, and their mixtures, with optional addition of the other surfactants mentioned, and in particular from decylglucoside, caprylyl/caprylglucoside, laurylglucoside, cocoglucoside, lauryl monophosphate, the potassium salt of dodecyl phosphate, the mixture of octyl phosphate monoester and diester, the potassium or triethanolamine salt of mono($C_{12}$–$C_{13}$)alkyl phosphate, potassium lauryl phosphate, and their mixtures.

Polymers

The amount of cationic and/or amphoteric polymer(s) in the composition of the invention can range, for example, from 0.01 to 5% by weight of active material and preferably from 0.1 to 2% by weight of active material, with respect to the total weight of the composition.

Use may be made of one or more cationic and/or amphoteric polymers. According to a preferred embodiment of the invention, the composition comprises at least one cationic polymer.

Cationic Polymers

Mention may be made, for example, as cationic polymers which can be used in the composition of the invention, of the polymers comprising at least one quaternary amine group and optionally primary, secondary, tertiary and/or quaternary amine groups forming part of the polymer chain or connected directly to the latter, the said polymers having a molecular weight ranging from 500 to approximately 5 000 000 and preferably from 1000 to 3 000 000. They are also characterized by a charge density ranging from 0.9 to 7 meq/g and preferably from 0.9 to 4 meq/g.

Mention may more particularly be made, among these polymers, of the following cationic polymers:

(1) homopolymers or copolymers obtained from one or more unsaturated monomers and comprising at least one quaternary ammonium group and in particular one of the units of following formulae:

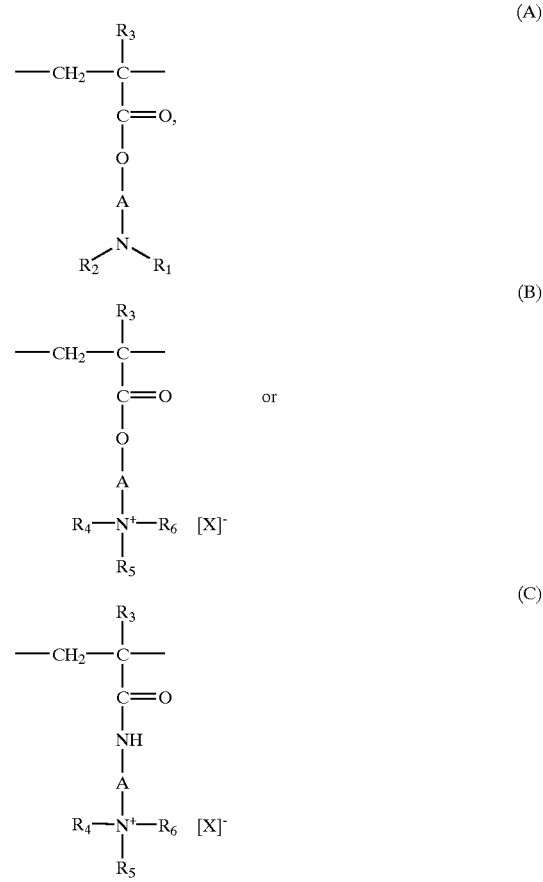

in which:
$R_3$ denotes a hydrogen atom or a $CH_3$ radical;
A is a linear or branched alkylene group comprising from 1 to 6 carbon atoms or a hydroxyalkylene group comprising from 1 to 4 carbon atoms;
$R_4$, $R_5$ and $R_6$, which are identical or different, represent an alkyl group having from 1 to 18 carbon atoms or a benzyl radical;
$R_1$ and $R_2$ represent a hydrogen atom or an alkyl group having from 1 to 6 carbon atoms;
X denotes a methyl sulphate anion or a halide, such as chloride or bromide.

The unsaturated monomer can be chosen from the group consisting of acrylamides, methacrylamides, diacetone acrylamides and acrylamides and methacrylamides substituted on nitrogen by alkyl radicals comprising from 1 to 8 carbon atoms, acrylic acid, methacrylic acid or their esters, vinyllactams, such as vinylpyrrolidone or vinylcaprolactam, vinyl esters, and their mixtures.

Thus, mention may be made, among these copolymers of the family (1), of, for example:
copolymers of acrylamide and of dimethylaminoethyl methacrylate quaternized with dimethylsulphate or with a dimethylhalide, such as the product sold under the name Hercofloc® by Hercules;
copolymers of acrylamide and of methacryloyloxyethyltrimethylammonium chloride, such as Polyquaternium 15 (CTFA name), for example sold under the name Rohagit KF 720 F® by Röhm & Haas;
the copolymer of acrylamide and of methacryloyloxyethyltrimethylammonium methyl sulphate, such as Polyquaternium 5 (CTFA name), for example sold under the name Merquat 5® by Calgon;

vinylpyrrolidone/dialkylaminoalkyl acrylate or methacrylate quaternized copolymers, such as Polyquaternium 11 (CTFA name), for example sold under the names Gafquat 755®, Gafquat 755N® and Gafquat 734® by ISP;

dimethylaminoethyl methacrylate/vinylcaprolactam/vinylpyrrolidone terpolymers, such as the product sold under the name Gaffix VC® 713 by ISP;

dimethylaminopropyl methacrylate/methacrylamide/vinylpyrrolidone terpolymers, such as Polyquaternium 28 (CTFA name), for example sold under the name Gafquat HS-100® by ISP;

copolymers based on vinylpyrrolidone and vinylcaprolactam, such as Polyquaternium 46 (CTFA name), for example sold under the name Luviquat Hold® by BASF;

(2) homopolymers or copolymers obtained from one or more unsaturated monomers and comprising a dimethyldiallylammonium radical of formula (IV) described below:

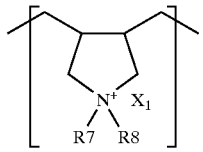

(IV)

in which:

$R_7$ and $R_8$, which are identical or different, denote a hydrogen atom or represent an alkyl group having from 1 to 18 carbon atoms;

$X_1$ denotes a methyl sulphate anion or a halide, such as chloride or bromide.

The unsaturated monomer can be chosen from the group consisting of acrylamides, methacrylamides, diacetone acrylamides, acrylamides and methacrylamides substituted on the nitrogen by alkyl radicals comprising from 1 to 8 carbon atoms, acrylic acid, methacrylic acid or their esters, vinyllactams, such as vinylpyrrolidone or vinylcaprolactam, vinyl esters, and their mixtures.

Thus, mention may be made, among the copolymers of the family (2), of, for example:

polymers of dimethyldiallylammonium chloride, such as Polyquaternium 6 (CTFA name), for example sold under the names Salcare SC 30® by Ciba and Merquat 100® by Calgon;

copolymers of acrylamide and of dimethyldiallylammonium chloride, such as Polyquaternium 7 (CTFA name), for example sold under the names Merquat S®, Merquat 2200® and Merquat 550® by Calgon and Salcare SC 10® by Ciba;

(3) quaternary copolymers of vinylpyrrolidone and of vinylimidazole, such as Polyquaternium 16 (CTFA name), for example sold under the names Luviquat FC905®, Luviquat FC370®, Luviquat HM552® and Luviquat FC550® by BASF, and Polyquaternium 44 (CTFA name), for example sold under the name Luviquat Care® by BASF;

(4) quaternized polysaccharides, such as:

guar or hydroxypropyl guar gums comprising trialkylammonium cationic groups, such as the products sold in particular under the trade names of Jaguar C13 S®, Jaguar C 15®, Jaguar C 17®, Jaguar C 162®, Jaguar C 2000® or Jaguar Excel®, by Meyhall;

quaternized cellulose derivatives, such as the hydroxyethylcellulose polymers comprising trialkylammonium and in particular trimethylammonium cationic groups, such as Polyquaternium 10 (CTFA name), for example sold under the names Ucare Polymer JR-400®, Ucare Polymer JR-125® or Ucare Polymer LR-400® by Amerchol; and such as cellulose derivatives grafted with a water-soluble monomer comprising a quaternary ammonium, in particular those disclosed in Patent U.S. Pat. No. 4,131,576, such as grafted hydroxyalkylcelluloses, for example hydroxymethyl-, hydroxyethyl- or hydroxypropylcelluloses grafted with a methacryloyloxyethyltrimethylammonium, methacrylamidopropyltrimethylammonium or dimethyldiallylammonium salt, more particularly the copolymer of hydroxyethylcellulose and of dimethyldiallylammonium chloride (CTFA name: Polyquaternium 4) sold under the names Celquat L 200® and Celquat H 100® by National Starch;

(5) chitosans or their salts, such as chitosan acetate, lactate, glutamate, gluconate or pyrrolidone carboxylate. Mention may in particular be made, among these compounds, of the chitosan having a degree of deacetylation of 90.5% by weight sold under the name Kytan Brut Standard® by Aber Technologies and the chitosan pyrrolidone carboxylate sold under the name Kytamer PC® by Amerchol; and (6) the blends of these cationic polymers.

The cationic polymers which are particularly preferred are Polyquaternium 5, Polyquaternium 7, Polyquaternium 28, Polyquaternium 39, Polyquaternium 44, and their blends, as they contribute great softness to the finished product, while leading, in the presence of silica, to optimum rinsing.

Amphoteric polymers

Mention may be made, as amphoteric polymers which can be used in the composition, of polymers comprising K and M units distributed randomly in the polymer chain, in which polymers K and M can have the following meanings:

1) K denotes a unit deriving from a monomer comprising at least one basic nitrogen atom and M denotes a unit deriving from an acidic monomer comprising one or more carboxylic or sulphonic groups; or else 2) K and M denote groups deriving from carboxybetaine or sulphobetaine zwitterionic monomers; or else 3) K and M denote a cationic polymer chain comprising primary, secondary, tertiary or quaternary amine groups, in which chain at least one of the amine groups carries a carboxylic or sulphonic group connected via a hydrocarbonaceous radical; or else 4) K and M form part of a chain of a polymer comprising an $\alpha,\beta$-dicarboxylic ethylene unit, one of the carboxylic groups of which has been reacted with a polyamine comprising one or more primary or secondary amine groups.

The amphoteric polymers which are more particularly preferred are chosen from the following polymers:

(1) polymers resulting from the copolymerization of a monomer derived from a vinyl compound carrying a carboxylic group, such as more particularly acrylic acid, methacrylic acid, maleic acid or $\alpha$-chloroacrylic acid, and of a basic monomer derived from a substituted vinyl compound comprising at least one basic atom, such as, more particularly, dialkylaminoalkyl methacrylates, dialkylaminoalkyl acrylates, dialkylaminoalkylmethacrylamides and dialkylaminoalkylacrylamides. Mention may be made, for example, of the sodium acrylate/ acrylamidopropyltrimethylammonium chloride copolymer sold under the name Polyquart KE 3033 by Henkel; or acrylic acid/methyl acrylate/ methacrylamidopropyltrimonium chloride terpolymers, such as Polyquaternium 47 (CTFA name), for example sold under the name Merquat 2001 N® by Calgon.

The vinyl compound can also be a dialkyldiallylammonium salt, such as diethyldiallylammonium chloride. The copolymers of acrylic acid and of diethyldiallylammonium chloride are, for example, those sold under the names Merquat 280®, Merquat 295® and Merquat Plus 3330® by Calgon.

(2) Polymers comprising units deriving:

a) from at least one monomer chosen from acrylamides or methacrylamides substituted on the nitrogen by an alkyl radical, in particular (N-alkyl)-substituted acrylamides or methacrylamides with alkyl radicals comprising from 2 to 12 carbon atoms, and more particularly N-ethylacrylamide, N-(tert-butyl)acrylamide, N-(tert-octyl)acrylamide, N-octylacrylamide, N-decylacrylamide, N-dodecylacrylamide, and the corresponding methacrylamides;

b) from at least one acidic comonomer comprising one or more reactive carboxylic groups, such as acrylic acid, methacrylic acid, crotonic acid, itaconic acid, maleic acid or fumaric acid, and the monoalkyl esters, the alkyl having 1 to 4 carbon atoms, of maleic acid, fumaric acid or maleic anhydride; and c) from at least one basic comonomer, such as esters comprising primary, secondary, tertiary and quaternary amine substituents of acrylic acid and methacrylic acid, and the quaternization product of dimethylaminoethyl methacrylate with dimethyl or diethyl sulphate. The preferred basic comonomers are aminoethyl methacrylate, butylaminoethyl methacrylate, N,N-dimethylaminoethyl methacrylate and N-(tert-butyl) aminoethyl methacrylate.

Mention may be made, as polymers comprising these units, of the product sold under the names Amphomer® or Lovocryl 47® by National Starch (CTFA name: Octylacrylamide/acrylate/butylaminoethyl methacrylate copolymer).

(3) Crosslinked and alkylated (partially or completely) polyaminoamides which are crosslinked by addition of a bifunctional crosslinking agent chosen from epihalohydrins, diepoxides, dianhydrides or bisunsaturated derivatives, by means of 0.025 to 0.35 mol of crosslinking agent per amine group of the polyaminoamide, and alkylated by the action of acrylic acid, of chloroacetic acid or of an alkanesultone or of their salts.

(4) Polymers comprising zwitterionic units of the formula (V):

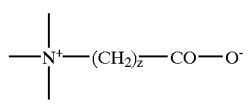

(V)

The polymers comprising such units can also comprise units derived from nonzwitterionic monomers, such as dimethylaminoethyl acrylate or methacrylate, diethylaminoethyl acrylate or methacrylate, alkyl acrylates or alkyl methacrylates, acrylamides or methacrylamides, or vinyl acetate.

Mention may be made, by way of example, of the methacryloylethyl N,N-dimethylcarboxymethyl betaine/ butyl methacrylate copolymer, such as the product sold under the name Diaformer Z301® by Sandoz.

(5) Amphoteric polymers derived from chitosan, such as the polymers derived from the N-carboxyalkylation of chitosan, for example the N-(carboxymethyl)chitosan or the N-(carboxybutyl)chitosan sold under the name Evalsan® by Jan Dekker.

(6) Amphoteric polymers derived from chloracetic acid or sodium chloracetate.

(7) ($C_1$–$C_5$)Alkyl vinyl ether/maleic anhydride copolymers in which a maleic anhydride is partially modified by semiamidation with an N,N-dialkylaminoalkylamine, such as N,N-dimethylaminopropylamine, or by semiesterification with an N,N-dialkanolamine. These copolymers can also comprise other vinyl comonomers, such as vinylcaprolactam.

Use may also be made of a blend of these amphoteric polymers or a blend of cationic amphoteric polymers.

The amphoteric polymers which are particularly preferred according to the invention are, for example, the products sold under the names Merquat 2001®, Merquat 280®, Merquat 295® and Merquat Plus 3330® by Calgon.

Aqueous medium in the composition according to the invention can comprise, in addition to water, one or more solvents chosen from lower alcohols comprising from 1 to 6 carbon atoms, such as ethanol; polyols, such as, for example, glycerol; glycols, such as butylene glycol, isoprene glycol, propylene glycol or polyethylene glycols, such as, PEG-8; sorbitol; sugars, such as glucose, fructose, maltose, lactose or sucrose; and their mixtures. The amount of solvent(s) in the composition of the invention can range, for example, from 0.5 to 30% by weight and preferably from 2 to 20% by weight with respect to the total weight of the composition.

The compositions of the invention can comprise adjuvants commonly used in the cosmetic field and in particular those used in cleansing products. Mention may be made, as adjuvants, of, for example, fragrances, preservatives, sequestering agents (EDTA), pigments, pearlescing agents, mattifying, whitening or exfoliating inorganic or organic fillers, soluble dyes, cosmetic or dermatological active principles, nonionic polymers, such as polyvinylpyrrolidone (PVP), anionic polymers, or fatty substances which are incompatible with the aqueous medium, such as oils or waxes. The amounts of these various adjuvants are those conventionally used in the field under consideration and are, for example, from 0.01 to 20% of the total weight of the composition. These adjuvants and their concentrations must be such that they do not modify the property desired for the composition of the invention.

Use may be made, as active principles, in the composition of the invention, of any active principle commonly used in the cosmetic and dermatological fields, such as, for example, water-soluble or fat-soluble vitamins or provitamins, such as vitamin A (retinol), vitamin C (ascorbic acid), vitamin B3 or PP (niacinamide), vitamin B5 (panthenol), vitamin E (tocopherol), vitamin K1 or β-carotene, and the derivatives of these vitamins and in particular their esters; steroids, such as DHEA and 7α-hydroxy-DHEA; antiseptic; antiseborrhoeics and antimicrobials, such as benzoyl peroxide, salicylic acid, triclosan, triclocarban or azelaic acid; moisturizing agents, such as glycerol, hyaluronic acid, pyrrolidonecarboxylic acid (PCA) and its salts, sodium pidolate, serine, xylitol, trehalose, ectoin, ceramides or urea; keratolytic and antiageing agents, such as α-hydroxy acids, for example glycolic acid, citric acid or lactic acid, or β-hydroxy acids, for example salicylic acid and its derivatives; enzymes and coenzymes and in particular coenzyme Q10; sunscreens; optical brighteners; slimming active principles, such as caffeine, theophylline or threobromine; antiinflammatories, such as 18-β-glycyrrhetinic acid and ursolic acid, and their mixtures. Use may be made of a mixture of two or more of these active principles. The active principle or principles can, for example, be present in a concentration ranging from 0.01 to 20%, preferably from 0.1 to 10% and better still from 0.5 to 5%, of the total weight of the composition.

Mention may be made, as fillers, of inorganic fillers, such as talc or magnesium silicate (particle size: 5 microns), sold under the name Luzenac 15 M00® by Luzenac, or kaolin or aluminium silicate, such as, for example, that sold under the name Kaolin Suprémé® by Imerys, or organic fillers, such as starch, as, for example, the product sold under the name Corn Starch B® by Roquette, Nylon microspheres, such as those sold under the name Orgasol 2002 UD NAT COS® by Atochem, or expanded microspheres based on vinylidene chloride/acrylonitrile/methacrylonitrile copolymer enclosing isobutane, such as those sold under the name Expancel 551 DE® by Expancel. Fibres, such as, for example, nylon fibres (Polyamide 0.9 dtex 0.3 mm, sold by Etablissements Paul Bonte) or cellulose or "Rayon" fibres (Rayon Flock RCISE NOOO3 MO4®, sold by Claremont Flock Corporation), can also be added to the composition of the invention.

The foaming compositions according to the invention can be used in the cosmetics and dermatological fields and they can constitute in particular products for cleansing or removing make-up from the skin (body, face, eyes), scalp and/or hair. They can be used for any skin type (dry, normal, mixed or greasy).

Another subject-matter of the invention is the cosmetic use of the composition as defined above as products for cleansing and/or removing make-up from the skin, eyes, scalp and/or hair.

The compositions according to the invention can also constitute a composition for disinfecting the skin and/or the scalp, in particular when they comprise an antibacterial agent. They can also be used for the treatment of greasy skin, in particular by adding thereto specific active principles for the treatment of greasy skin, such as antiseborrhoeics, as, for example, salicylic acid and its derivatives, azelaic acid, triclosan, triclocarban, piroctone olamine or niacinamide (vitamin PP).

Another subject-matter of the invention is the use of the composition as defined above in the preparation of a composition intended to disinfect the skin and/or the scalp.

Another subject-matter of the invention is a cosmetic process for cleansing the skin, eyes, scalp and/or hair, characterized in that the composition of the invention is applied to the skin, to the eyes, to the scalp and/or to the hair in the presence of water and in that the lather formed is removed by rinsing with water.

In the case of the cleansing of the face, the composition according to the invention can constitute a mask which is rinsed off after a leave-on time of 1 to 3 minutes.

The examples which follow serve to illustrate the invention without, however, exhibiting a limiting nature. The amounts indicated are as % by weight, unless otherwise mentioned. "A.M." means "active material". These examples are soap-free compositions.

EXAMPLES 1 TO 4 AND COMPARATIVE EXAMPLES 1 AND 2

Examples 1 to 4 and Comparative Examples 1 and 2 are presented in Table (4).

Comparative Example 1 corresponds to Example 1 or Example 2 according to the invention without cationic polymer and Comparative Example 2 corresponds to Example 2 according to the invention without silica.

The Comparative Examples are recorded as "Comp. Ex." in the following tables.

Examples 1 to 4 according to the invention differ from one another in the cationic polymer used.

TABLE (4)

| Compositon | Ex. 1 | Comp. EX. 1 | Ex. 2 | Comp. Ex. 2 | Ex. 3 | Ex. 4 |
|---|---|---|---|---|---|---|
| Lauryl monophosphate (Monoester: 75%) (MAP 20 from Kao) | 3.35 A.M. | 3.35 A.M. | 3.35 A.M. | 3.35 A.M. | 3.35 A.M. | 3.35 A.M. |
| Decylglucoside (Mydol 10 from Kao, comprising 40% A.M.) | 10.5 A.M. | 10.5 A.M. | 10.5 A.M. | 10.5 A.M. | 10.5 A.M. | 10.5 A.M. |
| Potassium hydroxide q.s. pH 7 | 0.9 | 0.9 | 0.9 | 0.9 | 0.9 | 0.9 |
| PEG-120 methylglucose dioleate (Glucamate DOE-120 V!e¦g!e¦tal from Amerchol) | 2 | 2 | 2 | 2 | 2 | 2 |
| Aerosil R-200 from Degussa (hydrophilic) | 5 | 5 | 5 | 0 | 5 | 5 |

TABLE (4)-continued

| Composition | Ex. 1 | Comp. EX. 1 | Ex. 2 | Comp. Ex. 2 | Ex. 3 | Ex. 4 |
|---|---|---|---|---|---|---|
| *Merquat 2001 N (Polyquaternium 47) | 0.5 A.M. | 0 | 0 | 0 | 0 | 0 |
| *Ucare Polymer JR-400 (Polyquaternium 10) | 0 | 0 | 0.5 A.M. | 0.5 A.M. | 0 | 0 |
| *Merquat 100 (Polyquaternium 6) | 0 | 0 | 0 | 0 | 0.5 A.M. | 0 |
| *Gafquat 755 N (Polyquaternium 11) | 0 | 0 | 0 | 0 | 0 | 0.5 A.M. |
| Preservatives | q.s. | q.s. | q.s. | q.s. | q.s. | q.s. |
| Demineralized water | q.s. for 100% | q.s. for 100% | q.s. for 100% | q.s. for 100% | q.s. for 100% | q.s. for 100% |
| Appearance | Homogeneous translucent soft gel | Homogeneous soft gel | Slightly translucent thick gel | Homogeneous smooth transparent gel | Homogeneous and smooth, soft opaque gel | Slightly translucent gel |
| pH | 7 | 6.8 | 7 | 7 | 6.9 | 7 |
| Viscosity at 25° C. Rheomat 180 | 92 P (R 4) | 111 P (R 4) | 184 P (R 4) | 43 P (R 4) | 45 P (R 4) | 54 P (R 4) |

*Merquat 2001 N: Acrylic acid/methacrylamido-propyltrimonium chloride/methylacrylate terpolymer as a 20% aqueous solution, sold by Calgon. CTFA name: Polyquaternium 47.
*Ucare Polymer JR-400: Hydroxyethylcellulose quaternized with 2,3-epoxypropyltrimethylammonium chloride, sold by Amerchol. CTFA name: Polyquaternium 10.
*Merquat 100: Poly(dimethyldiallylammonium chloride) at 40% in water, sold by Calgon. CTFA name: Polyquaternium 6.
*Gafquat 755 N: Vinylpyrrolidone/dimethylaminoethyl methacrylate copolymer, the dimethylaminoethyl methacrylate being quaternized with dimethylsulphate, at 20% in water, sold by ISP. INCI name: Polyquaternium 11.

Sensory performances: the foaming qualities developed by the compositions defined above were evaluated according to the protocol described below.

Before any use of the products, the hands are washed with household soap and then suitably rinsed and dried. The protocol followed is then as follows:

1—the hands are wetted by passing them under running water and shaking them three times to drain the water off them, 2—1 g of product is placed in the hollow of one of the hands, 3—the product is worked between the two palms for 10 seconds, 4—2 ml of water are added and the product is again worked for 10 seconds, 5—the hands are rinsed under water, 6—they are dried.

The criteria are evaluated at each stage of the protocol followed and they are graded on a scale from 0 to 10. For a given criteria, a difference in grade between two compositions is regarded as existing when this difference is greater than or equal to 1.

Stage 3:
evaluation of slippery on spreading: the grade assigned becomes higher as the feeling of slippery on the wet hands becomes greater.

evaluation of mixing with water: the grade assigned becomes higher as the mixing of the product with water becomes easier.

evaluation of homogeneity: the grade assigned becomes higher as the film formed by the product on the hand becomes more homogeneous.

evaluation of the covering power: the grade assigned becomes higher as the skin of the hand becomes more difficult to see through the product spread over the skin.

Stage 4:
Evaluation of the Foaming Quality
The volume of lather: the grade assigned increases as the volume increases and therefore the product is better when the grade is high.

The size of the bubbles composing the lather: the grade assigned increases as the bubbles become larger and therefore the product is better when the grade is low.

The density: consistency, behaviour of the lather: the grade assigned increases as the density increases and therefore the product is better when the grade is high.

The softness of the lather: the grade assigned increases as the lather becomes softer and therefore the product is better when the grade is high.

Stage 5:
Evaluation During Rinsing
The rinsing: the grade assigned decreases as the presence of a slippery film which is difficult to remove increases and therefore the product is better when the grade is high.

The sensory results for each of the criteria are presented in the following Table (5):

TABLE (5)

|  | Ex. 1 | Comp. Ex. 1 | Ex. 2 | Comp. Ex. 2 | Ex. 3 | Ex. 4 |
|---|---|---|---|---|---|---|
| Slippery on spreading | 7.8 | 7.7 | 7.5 | 7.8 | 7.2 | 8.2 |
| Mixing with water | 7.5 | 7.2 | 6.3 | 7.0 | 7.5 | 6.2 |
| Homogeneity | 5.7 | 7.0 | 5.5 | 5.8 | 7.5 | 6.0 |
| Covering power | 6.5 | 7.0 | 6.3 | 7.5 | 7.0 | 7.0 |
| Volume of the lather | 4.3 | 5.3 | 4.8 | 5.0 | 5.8 | 5.3 |
| Size of the bubbles | 4.0 | 4.7 | 3.8 | 3.5 | 5.5 | 3.1 |
| Density | 7.0 | 7.5 | 7.5 | 9.0 | 6.7 | 7.3 |
| Softness of the lather | 7.8 | 7.0 | 7.1 | 8.5 | 6.7 | 7.5 |
| Rinsing | 9.7 | 9.7 | 8.3 | 6.3 | 9.7 | 10 |

The examples described above demonstrate the positive influence of the silica on the rinsing of the compositions based on cationic polymers. Thus, despite the presence of the polymers Polyquaternium 47, Polyquaternium 6 and Polyquaternium 11, Examples 1, 3 and 4 according to the invention have very good rinsing (grade of 9.7 or 10), equivalent to that of Comparative Example 1, which does not comprise polymer, although these polymers are known to effect the quality of the rinsing.

In the case of Polyquaternium 10, which is known for its film-forming finish, Example 2 shows that the silica makes it possible to significantly improve the rinsing with respect to Comparative Example 2, which does not comprise silica, since the rinsing grade is then 8.3 instead of 6.3, while retaining satisfactory softness.

EXAMPLES 5 AND 6 AND COMPARATIVE EXAMPLES 3 TO 9 composition based on Polyquaternium 7 (copolymer of acrylamide and of dimethyldiallylammonium chloride). These examples are presented in Table (6).

Examples 5 and 6 differ from one another in the type of silica used and in the presence of glycerol in Example 6.

Comparative Examples 3 and 4 are to be compared with Examples 5 and 6, Comparative Examples 5 to 7 are to be compared with Example 5, and Comparative Examples 8 and 9 are to be compared with Example 6:

Comparative Ex. 3: corresponds to Example 5 or 6 without silica or cationic polymer.

Comparative Ex. 4: corresponds to Example 5 or 6 without silica.

Comparative Ex. 5: corresponds to Example 5 without cationic polymer or oxyethylenated compound.

Comparative Ex. 6: corresponds to Example 5 without cationic power.

Comparative Ex. 7: corresponds to Example 5 without oxyethylenated compound.

Comparative Ex. 8: corresponds to Example 6 without cationic polymer or oxyethylenated compound.

Comparative Ex. 9: corresponds to Example 6 without cationic polymer.

TABLE (6)

| Compositions | Comp. Ex. 3 | Comp. Ex. 4 | Comp. Ex. 5 | Comp. Ex. 6 |
|---|---|---|---|---|
| Decylglucoside (Mydol 10 from Kao, comprising 40% of A.M.) | 6.5% A.M. | 6.5% A.M. | 6.5% A.M. | 6.5% A.M. |

TABLE (6)-continued

| Lauryl monophosphate (MAP 20 from Kao) | 6.5% A.M. | 6.5% A.M. | 6.5% A.M. | 6.5% A.M. |
|---|---|---|---|---|
| PEG-120 methylglucose dioleate (Gucamate DOE-120 Végétal from Amerchol) | 2 | 2 | 0 | 2 |
| Polyquaternium 7 (Merquat S from Calgon) | 0 | 0.5% A.M. | 0 | 0 |
| Aerosil R-200 (hydrophilic) | 0 | 0 | 5 | 5 |
| Aerosil R-972 (hydrophobic) | 0 | 0 | 0 | 0 |
| Glycerol | 0 | 0 | 0 | 0 |
| Preservatives | q.s. | q.s. | q.s. | q.s. |
| Potassium hydroxide q.s. pH 7 | 1.7 | 1.7 | 1.7 | 1.7 |
| Water | q.s. for 100% | q.s. for 100% | q.s. for 100% | q.s. for 100% |
| Viscosity at T0* at 25° C. Rheomat 180 | 95 P (R 4) | 165 P (R 4) | 9.1 P (R 3) | 156 P (R 4) |
| Stability | Yes | Yes | No | Yes |

| Compositions | Comp. Ex. 7 | Ex. 5 | Comp. Ex. 8 | Comp. Ex. 9 | Ex. 6 |
|---|---|---|---|---|---|
| Decylglucoside (Mydol 10 from Kao, comprising 40% of A.M.) | 6.5% A.M. | 6.5% A.M. | 6.5% A.M. | 6.5% A.M. | 6.5% A.M. |
| Lauryl monophosphate (MAP 20 from Kao) | 6.5% A.M. | 6.5% A.M. | 6.5% A.M. | 6.5% A.M. | 6.5% A.M. |
| PEG-120 methylglucose dioleate (Gucamate DOE-120 Végétal from Amerchol) | 0 | 2 | 0 | 2 | 2 |
| Polyquaternium 7 (Merquat S from Calgon) | 0.5% A.M. | 0.5% A.M. | 0 | 0 | 0.5% A.M. |
| Aerosil R-200 (hydrophilic) | 5 | 5 | 0 | 0 | 0 |
| Aerosil R-972 (hydrophobic) | 0 | 0 | 5 | 5 | 5 |
| Glycerol | 0 | 0 | 0 | 0 | 3.5 |
| Preservatives | q.s. | q.s. | q.s. | q.s. | q.s. |
| Potassium hydroxide q.s. pH 7 | 1.7 | 1.7 | 1.7 | 1.7 | 1.7 |
| Water | q.s. for 100% | q.s. for 100% | q.s. for 100% | q.s. for 100% | q.s. for 100% |
| Viscosity at T0 at 25° C. Rheomat 180 | Not measurable | 161 P (R 4) | <130 cP (R 2) | 142 P (R 4) | 104 P (R 4) |
| Stability | No | Yes | No | Yes | Yes |

*T0 means at time zero

In the above table, P means poises, cP means centipoises and R indicates the rotor for measuring the viscosity (R4=rotor 4; R3=rotor 3 and R2=rotor 2).

The examples have the following appearance:

Comparative Example 3: Homogeneous translucent fairly thick gel;

Comparative Example 4: Homogeneous translucent fairly thick gel;

Comparative Example 5: Off-white opaque soft paste;

Comparative Example 6: Slightly translucent very thick gel;

Comparative Example 7: Granular gel with immediate separation during manufacture;

Example 5 according to the invention: Slightly translucent homogeneous very thick gel;

Comparative Example 8: White opaque solution;

Comparative Example 9: Slightly translucent homogeneous very thick gel;

Example 6 according to the invention: Slightly translucent homogeneous soft thick gel.

The above table shows that:

Example 5 exhibits good stability, in contrast to Comparative Example 5, which comprises neither oxyethylenated compound nor cationic polymer, and in comparison with Comparative Example 7, which does not comprise oxyethylenated compound.

Example 6 exhibits good stability, in contrast to Comparative Example 8, which comprises neither oxyethylenated compound nor cationic polymer.

Sensory performances: they were evaluated according to the protocol described above.

The results are shown in the following Table (7):

TABLE (7)

|  | Comp. Ex. 3 | Comp. Ex. 4 | Comp. Ex. 5 | Comp. Ex. 6 |
|---|---|---|---|---|
| Mixing with water | 6.5 | 8.2 | 8.9 | 7.3 |
| Covering power | 6.8 | 7 | 6.3 | 7.1 |
| Volume of the lather | 5.6 | 6 | 5.8 | 5.5 |
| Size of the bubbles | 3.9 | 4.1 | 3.6 | 3.5 |
| Density | 7.5 | 8 | 7 | 7 |
| Softness of the lather | 6.8 | 8.2 | 5.3 | 6.6 |
| Rinsing | 8.9 | 8.3 | 9.1 | 9.3 |

|  | Ex. 5 | Comp. Ex. 8 | Comp. Ex. 9 | Ex. 6 |
|---|---|---|---|---|
| Mixing with water | 9.2 | 10 | 7.5 | 10 |
| Covering power | 8.8 | 6.1 | 6.5 | 9.4 |
| Volume of the lather | 6.3 | 5.5 | 6.1 | 6.8 |
| Size of the bubbles | 4.1 | 4.1 | 3.8 | 3.9 |
| Density | 8 | 6.8 | 7.1 | 7.9 |
| Softness of the lather | 8.3 | 6 | 5.8 | 8.6 |
| Rinsing | 9.5 | 9.1 | 9.6 | 9.3 |

A marked improvement in the covering power is observed for the compositions according to the invention: the covering power of Examples 5 and 6 is markedly better than that of the comparative examples. The best volume of lather is also obtained with the compositions according to the invention.

Furthermore, the addition of hydrophilic silica (Example 5) or hydrophobic silica (Example 6) makes possible better rinsing than Comparative Example 4, comprising the cationic polymer (Merquat S) without silica.

Furthermore, a synergistic effect as regards the mixing with water is observed for the products in which hydrophilic silica, cationic polymer and oxyethylenated compound are combined: this is because Example 5 has a better ability to mix with water than Comparative Examples 3, 4 and 6, which renders the product easier to employ.

EXAMPLES 7 TO 10 ACCORDING TO THE INVENTION

These examples are presented in the following Table (8).

Examples 7, 9 and 10 constitute a foaming product which can be used in particular for cleansing the face. Example 8 constitutes a foaming mask.

TABLE (8)

| Compositions | Example 7 | Example 8 | Example 9 | Example 10 |
|---|---|---|---|---|
| Decylglucoside (Mydol 10 from Kao, comprising 40% of A.M.) | 6.5% A.M. | 6.5% A.M. | 6.5% A.M. | 6.5% A.M. |
| Lauryl monophosphate (MAP 20 from Kao) | 6.5% A.M. | 6.5% A.M. | 6.5% A.M. | 6.5% A.M. |
| SER Ad Fx 1100 | 0 | 0 | 2% | 2% |
| PEG-120 methylglucose dioleate (Glucamate DOE-120 Vegetal from Amerchol) | 2% | 2% | 0 | 0 |
| Polyquaternium 7 (Merquat S from Calgon) | 0.5% A.M. | 0.5% A.M. | 0.5% A.M. | 0.5% A.M. |
| Aerosil R-200 (hydrophilic) | 5 | 5 | 5 | 0 |
| Aerosil R-972 (hydrophobic) | 0 | 0 | 0 | 5 |
| Corn starch B(1) | 0 | 10 | 0 | 0 |
| Polyamide 0.9 dtex 0.3 mm (2) | 5 | 0 | 0 | 0 |
| Preservatives | q.s. | q.s. | q.s. | q.s. |
| Potassium hydroxide q.s. pH 7 | 1.7 | 1.7 | 1.7 | 1.7 |
| Water | q.s. for 100% | q.s. for 100% | q.s. for 100% | q.s. for 100% |
| Appearance | Smooth white cream gel | Smooth and white cream gel | Homogeneous opaque very thick gel | Homogeneous opaque thick gel |
| Viscosity at T0 at 25° C. Rheomat 180 | 109 P (R 4) | 100 P (R 4) | >236 P (R 4) | 212 P (R 4) |

In the above Table (8), P means poises and R indicates the rotor for measuring the viscosity (R4=rotor 4).

(1) Corn starch B: corn starch: amylopectin/amylose or "*Zea mays* (corn) starch", sold by Roquette.

(2) Polyamide 0.9 dtex 0.3 mm: 0.9 dtex polyamide fibres with a length of 0.3 mm, washed under hot conditions and then buffered, or Nylon-66, sold by Etablissements Paul Bonte.

French patent application 0109767 filed Jul. 20, 2001, is hereby incorporated herein by reference, as are all texts, references, tests, documents, publications, applications and patents referred to above.

What is claimed is:

1. A physiologically acceptable composition comprising, water and:
   (1) at least one foaming surfactant,
   (2) at least 1% by weight of at least one silica, with respect to the total weight of the composition,
   (3) at least one oxyalkylenated compound selected from the group consisting of polyethylene glycol (150 EO) distearate, polyethylene glycol (250 EO) distearate, PEG-150 dibehenate, polyethylene glycol (120 EO) palmitostearate, oxyethylenated (120 EO) methylglucose dioleate, oxyethylenated (150 EO) pentaerythrityl tetrastearate, the oxyethylenated (100 EO) stearyl alcohol/polyethylene glycol (136 EO)/hexamethylene diisocyanate copolymer, and mixtures thereof, and
   (4) at least one polymer selected from the group consisting of cationic polymers, amphoteric polymers and mixtures thereof.

2. The composition according to claim 1, comprising at least 35% by weight of water with respect to the total weight of the composition.

3. The composition according to claim 1, comprising from 35 to 95% by weight of water with respect to the total weight of the composition.

4. The composition according to claim 1, wherein said composition has a viscosity of from 0.5 to 25 Pa.s.

5. The composition according to claim 1, wherein the amount of silica is from 1 to 15% by weight with respect to the total weight of the composition.

6. The composition according to claim 1, wherein the silica is selected from the group consisting of hydrophilic silicas, hydrophobic silicas, and mixtures thereof.

7. The composition according to claim 1, comprising hydrophilic silica selected from the group consisting of silicas of pyrogenic origin, silicas of precipitated origin and mixtures thereof.

8. The composition according to claim 1, comprising hydrophilic silica selected from the group consisting of silicas having a specific surface of 30 to 500 $m^2/g$, a number-average particle size ranging from 3 to 50 nm, and a tamped density ranging from 40 to 200 g/l.

9. The composition according to claim 1, comprising pyrogenic silica.

10. The composition according to claim 1, comprising hydrophilic silica consisting of a particle coated with hydrophilic silica.

11. The composition according to claim 1, comprising amorphous silica of pyrogenic origin.

12. The composition according to claim 1, comprising hydrophobic silica selected from the group consisting of silicas having a specific surface of 50 to 500 $m^2/g$, a number-average particle size ranging from 3 to 50 nm, and a tamped density ranging from 40 to 200 g/l.

13. The composition according to claim 1, wherein the at least one oxyalkylenated compound is present in an amount of from 0.1 to 20% by weight of active material with respect to the total weight of the composition.

14. The composition according to claim 1, wherein the foaming surfactant is selected from the group consisting of nonionic surfactants, anionic surfactants, amphoteric and zwitterionic surfactants, and mixtures thereof.

15. The composition according to claim 1, wherein the amount of foaming surfactant is present in an amount of from 2 to 50% by weight of active material with respect to the total weight of the composition.

16. The composition according to claim 1, comprising a foaming surfactant selected from the group consisting of alkylpolyglucosides, maltose esters, polyglycerolated fatty alcohols, glucamine derivatives, carboxylates, amino acid derivatives, alkyl sulphates, alkyl ether sulphates, sulphonates, isethionates, taurates, sulphosuccinates, alkyl sulphoacetates, phosphates and alkyl phosphates, polypeptides, anionic alkylpolyglucoside derivatives, fatty acid soaps, betaines, N-alkylamidobetaines and their derivatives, glycine derivatives, sultanes, alkyl polyaminocarboxylates, alkylamphoacetates, and mixtures thereof.

17. The composition according to claim 1, comprising a foaming surfactant selected from the group consisting of decylglucoside, caprylyl/caprylglucoside, laurylglucoside, cocoglucoside, lauryl monophosphate, the potassium salt of dodecyl phosphate, the mixture of octyl phosphate monoester and diester, the potassium or triethanolamine salt of mono ($C_{12}$–$C_{13}$)alkyl phosphate, potassium lauryl phosphate, and mixtures thereof.

18. The composition according to claim 1, wherein the amount of cationic and/or amphoteric polymer is present in an amount of from 0.01 to 5% by weight of active material with respect to the total weight of the composition.

19. The composition according to claim 1, comprising a cationic polymer having a molecular weight of from 500 to 5 000 000.

20. The composition according to claim 1, comprising a cationic polymer having a charge density of from 0.9 to 7 meq/g.

21. The composition according to claim 1, comprising a cationic polymer selected from the group consisting of:
(1) homopolymers or copolymers obtained from one or more unsaturated monomers and comprising at least one quaternary ammonium group, having one of the following formulae:

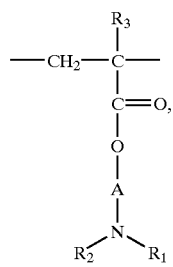

(A)

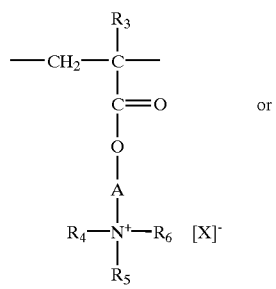 or (B)

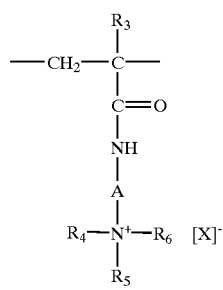

(C)

in which:
$R_3$ denotes a hydrogen atom or a $CH_3$ radical;
A is a linear or branched alkylene group comprising from 1 to 6 carbon atoms or a hydroxyalkylene group comprising from 1 to 4 carbon atoms;
$R_4$, $R_5$ and $R_6$, which are identical or different, represent an alkyl group having from 1 to 18 carbon atoms or a benzyl radical;
$R_1$ and $R_2$ represent a hydrogen atom or an alkyl group having from 1 to 6 carbon atoms;
X denotes a methyl sulphate anion or a halide, such as chloride or bromide;
(2) homopolymers or copolymers obtained from one or more unsaturated monomers and comprising a dimethyldiallylammonium radical;
(3) quaternary copolymers of vinylpyrrolidone and of vinylimidazole;
(4) quaternized polysaccharides;

(5) chitosans or their salts; and (6) mixtures thereof.

22. The composition according to claim 1, comprising a cationic polymer selected from the group consisting of copolymers of acrylamide and of dimethylaminoethyl methacrylate quaternized with dimethyl sulphate or with a dimethyl halide, copolymers of acrylamide and of methacryloyloxyethyltrimethylammonium chloride, the copolymer of acrylamide and of methacryloyloxyethyltrimethylammonium methyl sulphate, vinylpyrrolidone/dialkylaminoalkyl acrylate or methacrylate quaternized copolymers, dimethylaminoethyl methacrylate/vinylcaprolactam/vinylpyrrolidone terpolymers, dimethylaminopropyl methacrylate/methacrylamide/vinylpyrrolidone terpolymers, copolymers based on vinylpyrrolidone and vinylcaprolactam, dimethyldiallylammonium chloride polymers, copolymers of acrylamide and of dimethyldiallylammonium chloride, guar or hydroxypropyl guar gums comprising trialkyl-ammonium cationic groups, quaternized cellulose derivatives, and mixtures thereof.

23. The composition according to claim 1, comprising a cationic polymer selected from the group consisting of Polyquaternium 5, Polyquaternium 7, Polyquaternium 28, Polyquaternium 39, Polyquaternium 44, and mixtures thereof.

24. The composition according to claim 1, wherein the polymer is an amphoteric polymer selected from the group consisting of polymers comprising K and M units distributed randomly in the polymer chain, in which polymers K and M have the following meaning:

K denotes a unit deriving from a monomer comprising at least one basic nitrogen atom and M denotes a unit deriving from an acidic monomer comprising one or more carboxylic or sulphonic groups; or else K and M denote groups deriving from carboxybetaine or sulphobetaine zwitterionic monomers; or K and M denote a cationic polymer chain comprising primary, secondary, tertiary or quaternary amine groups, in which chain at least one of the amine groups carries a carboxylic or sulphonic group connected via a hydrocarbonaceous radical; or K and M form part of a chain of a polymer comprising an α,β-dicarboxylic ethylene unit, one of the carboxylic groups of which has been reacted with a polyamine comprising one or more primary or secondary amine groups.

25. The composition according to claim 1, comprising an amphoteric polymer selected from the group consisting of dialkylaminoalkyl methacrylates and acrylates; dialkylaminoalkylmethacrylamides and dialkylaminoalkylacrylamides; copolymers of acrylic acid and of diethyldiallylammonium chloride; and mixtures thereof.

26. The composition according to claim 1, comprising an amphoteric polymer selected from the group consisting of polymers comprising polymerized units of:

a) at least one monomer selected from the group consisting of acrylamides or methacrylamides substituted on the nitrogen by an alkyl radical comprising from 2 to 12 carbon atoms, b) at least one acidic comonomer comprising one or more reactive carboxylic groups, and c) at least one basic comonomer.

27. The composition according to claim 1, comprising an amphoteric polymer selected from the group consisting of crosslinked and alkylated polyaminoamides; polymers comprising zwitterionic units of formula (V)

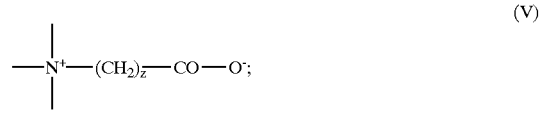

amphoteric polymers derived from chitosan; amphoteric polymers derived from chloroacetic acid or sodium chloroacetate; ($C_1$–$C_5$) alkyl vinyl ether/maleic anhydride copolymers, the maleic anhydride being partially modified by semiamidation with an N,N-dialkylaminoalkylamine; and mixtures thereof.

28. The composition according to claim 1, comprising an acrylic acid/methyl acrylate/methacryl amidopropyltrimonium chloride terpolymer or Polyquaternium 47 or both.

29. The composition according to claim 1, further comprising at least one solvent selected from the group consisting of alcohols comprising from 1 to 6 carbon atoms, polyols, and mixtures thereof.

30. The composition according to claim 1, further comprising at least one active principle selected from the group consisting of water-soluble or fat-soluble vitamins or provitamins and their derivatives; steroids; antiseptics; antiseborrhoeics; antimicrobials; moisturizing agents; keratolytic and antiageing agents; enzymes and coenzymes; sunscreens; optical brighteners; slimming active principles; antiinflammatories; and mixtures thereof.

31. The composition according to claim 1, further comprising an active principle is selected from the group consisting of vitamin A, vitamin C, vitamin B3, vitamin B5, vitamin E, vitamin K1, β-carotene, and their derivatives; DHEA and 7α-hydroxy-DHEA; benzoyl peroxide, salicylic acid, triclosan, triclocarban or azelaic acid; glycerol, hyaluronic acid, pyrrolidonecarboxylic acid and its salts, serine, xylitol, trehalose, ectoin, ceramides or urea; glycolic acid, citric acid, lactic acid, salicylic acid and its derivatives; coenzyme Q10; 18-β-glycyrrhetinic acid, ursolic acid, and mixtures thereof.

32. The composition according to claim 1, further comprising at least one filler.

33. The composition according to claim 1, in the form of a mask.

34. A method for cleansing and/or removing make-up from the skin, eyes, scalp and/or hair, comprising applying the composition of claim 1, thereto.

35. A method of disinfecting the skin and/or the scalp, comprising applying a disinfecting effective amount of the composition of claim 1, to the skin and/or the scalp.

36. A process for cleansing the skin, eyes, scalp and/or hair, comprising:

applying the composition according to claim 1, to the skin, to the eyes, to the scalp and/or to the hair in the presence of water to form a lather, and removing the lather by rinsing with water.

* * * * *